(12) United States Patent
Nakagawa

(10) Patent No.: US 11,027,142 B2
(45) Date of Patent: Jun. 8, 2021

(54) METABOLIC BASED PREDICTION METHOD FOR A SUCCESSFUL DEFIBRILLATION

(71) Applicant: KONINKLIJKE PHILIPS N.V., Eindhoven (NL)

(72) Inventor: Michael Nakagawa, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 29 days.

(21) Appl. No.: 15/086,111

(22) PCT Filed: Mar. 29, 2016

(86) PCT No.: PCT/IB2016/051757
§ 371 (c)(1),
(2) Date: Mar. 31, 2016

(87) PCT Pub. No.: WO2016/157071
PCT Pub. Date: Oct. 6, 2016

(65) Prior Publication Data
US 2018/0008835 A1 Jan. 11, 2018

Related U.S. Application Data

(60) Provisional application No. 62/140,874, filed on Mar. 31, 2015.

(51) Int. Cl.
*A61N 1/39* (2006.01)
(52) U.S. Cl.
CPC ......... *A61N 1/3987* (2013.01); *A61N 1/3904* (2017.08); *A61N 1/3925* (2013.01)
(58) Field of Classification Search
CPC ... A61N 1/3987; A61N 1/3904; A61N 1/3925
See application file for complete search history.

(56) References Cited

U.S. PATENT DOCUMENTS

| | | | |
|---|---|---|---|
| 5,957,856 A | 9/1999 | Bisera et al. | |
| 2005/0043675 A1* | 2/2005 | Pastore | A61B 5/0031 604/67 |

(Continued)

OTHER PUBLICATIONS

Shandilya, S. et al., "Non-linear dynamical signal characterization for prediction of defibrillation success through machine learning", BMC Medical Informatics and Decision Making 2012, 12:116.

(Continued)

*Primary Examiner* — Catherine M Voorhees
*Assistant Examiner* — Roland Dinga

(57) ABSTRACT

A system employing an ECG monitor (40) and a defibrillation advisory controller (20). In operation, the ECG monitor (40) monitors a cardiac rhythm of a patient, and the defibrillation advisory controller (20) generates a defibrillation advisory based on a cardiac rhythm status and a metabolic cardiac status of the patient, and optionally further based on an electrical cardiac status of the patient. The controller (20) derives the cardiac rhythm status as monitored by ECG monitor (40), and the optional electrical cardiac status inclusive of the cardiac rhythm monitored by the ECG monitor (40), and derives the metabolic cardiac status exclusive of the cardiac rhythm monitored by the ECG monitor (40). The controller (20) may compute or receive metabolic cardiac data indicative of the metabolic cardiac status (e.g., incorporating or coupled to a user input device (50), a breath analyzer (60) and a blood analyzer (70)), and compares the metabolic cardiac data to a metabolic cardiac threshold (fixed or variable) and/or monitors a trend of the metabolic cardiac data to derive the metabolic cardiac status of the patient.

20 Claims, 4 Drawing Sheets

(56) References Cited

U.S. PATENT DOCUMENTS

| | | | |
|---|---|---|---|
| 2006/0173499 A1* | 8/2006 | Hampton | A61N 1/3925 |
| | | | 607/5 |
| 2008/0169624 A1 | 7/2008 | Hon | |
| 2011/0202101 A1 | 8/2011 | Bures et al. | |
| 2013/0331719 A1 | 12/2013 | Freeman et al. | |
| 2015/0080670 A1* | 3/2015 | Osorio | A61B 5/7275 |
| | | | 600/301 |
| 2015/0297903 A1 | 10/2015 | Kantor et al. | |

OTHER PUBLICATIONS

Eilevstjonn, J. et al., "Shock outcome is related to prior rhythm and duration of ventricular fibrillation", Resuscitation (2007) 75, 60-67.
Klabunde, Richard E., PhD, "Cardiovascular Physiology Concepts" Chapter 3, Cardiac Myocyte Metabolism, p. 50.
Nik, L. et al., "Delaying defibrillation to give basic cardiopulmonary resuscitation to patients with out-of-hospital ventricular fibrillation", Journal American Medical Association, Mar. 19, 2003, vol. 289, No. 11, p. 1389-1395.
Cobb, L.A. et al., "Influence of cardiopulmonary resuscitation prior to defibrillation in patients with out-of-hospital ventricular fibrillation", Journal American Medical Association, Apr. 7, 1999, vol. 281, No. 13, p. 1182-1188.
Firoozabadi, R. et al., "Predicting defibrillation success in sudden cardiac arrest patients", Journal of Electrocardiology, 46 (2013) 473-479.
Kern, K.B. et al., "Depletion of myocardial adenosine triphosphate during prolonged untreated ventricular fibrillation: effect on defibrillation success", Resuscitation, 20 (1990) 221-229.

\* cited by examiner

METABOLIC BASED PREDICTION METHOD FOR A SUCCESSFUL DEFIBRILLATION

FIELD OF THE INVENTION

The present invention generally relates to systems incorporated within medical devices/systems for cardiac resuscitation (e.g., internal defibrillators and external defibrillators, particularly advanced defibrillator/monitors and automated external defibrillators). The present invention specifically relates to predicting a successful defibrillation of a patient by combining independent information on electrical activity and aerobic metabolism of the patient's heart.

BACKGROUND OF THE INVENTION

Generally, ventricular fibrillation ("VF") and ventricular tachycardia ("VT") are cardiac arrhythmia conditions of a patient involving abnormal cardiac rhythms that may lead to irreversible cardiac arrest unless resuscitation procedures are properly applied to the patient. Defibrillation is one such resuscitation procedure and involves a therapeutic application of an electrical shock to the patient to restore normal perfusing cardiac rhythm. Of importance is an improper application of such an electrical shock may delay or prevent recovery by the patient if the electrical shock does not induce conversion of the abnormal heart rhythm to normal perfusing cardiac rhythm. Thus, to minimize, if not prevent, improper defibrillation of the patient, electrocardiogram ("ECG") based prediction methods for predicting successful defibrillation have been developed. These prediction methods have proven to have a limited success rate.

Specifically. ECG-only analyses measure voltages from cell membrane activity, which can give an indication of overall cell viability. However, activation of the cell membrane does not necessarily give an indication of the state of actin-myosin within cell. An insufficient supply of high energy phosphate compounds within the cell (adenosine triphosphate ("ATP") and creatine phosphate) can leave the actin and myosin chains locked in rigor, although the cell may be able to generate an action potential that contributes to the cumulative ECG. As highlighted in cases of pulseless electrical activity ("PEA"), ECG activity does not result in mechanical contractions of the heart, limiting the usefulness of ECG as an indicator for myocardial status.

SUMMARY OF THE INVENTION

The present invention is premised on a recognition that independent measurement of the byproducts of metabolism can support ECG rhythm analysis in determining the effectiveness of shock delivery for restoring a pulsatile rhythm. Discouraging or preventing shocks when the myocardium cannot support a pulsatile rhythm may allow continued recovery, rather than depleting the limited supply of ATP as cells start to restore their functioning.

More particularly, whether fibrillation should always be shocked to reduce metabolic activity or if cardiopulmonary resuscitation ("CPR") should be employed before shocks to re-establish metabolic sufficiency before shock delivery may depend on whether the heart was recently perfusing but is degrading, or whether the heart is recovering after an extended period of ischemia. Determining a trend in a metabolic cardiac status of the patient may indicate if the status is improving or degrading, while the actual instantaneous measurement may indicate if there is a minimum threshold level of activity that may support successful defibrillation. The present invention provides inventive principles directed to using an independent measurement of metabolic activity level in addition to an electrical activity level is a new feature that could minimize inappropriate shocks that could set back the recovery process. Combining ECG and independent metabolic analysis could maximize the effort of restoring overall cell viability without energy depleting shocks and time to deliver them.

The present invention incorporates the understanding that cellular metabolism must support the mechanical contractions deep within the cells in addition to electrical activity of the membrane, which generates the ECG signal, highlighting the need for measuring more than just electrical activity to determine the metabolic state of the cardiac cells during resuscitation. Since measures of metabolic state that are based only on electrical activity of the cell membranes may not truly reflect the probability of restoring a pulsatile rhythm with a defibrillation shock, the addition of a more direct measure of metabolic state of the myocardium into the analysis of patient condition would help with patient recovery.

One form of the present invention is a system employing an ECG monitor and a defibrillation advisory controller. In operation, the ECG monitors a cardiac rhythm of a patient, and the defibrillation advisory controller generates a defibrillation advisory based on a cardiac rhythm status and a metabolic cardiac status of the patient. The defibrillation advisory controller derives the cardiac rhythm status as monitored by the ECG monitor, and derives the metabolic cardiac status exclusive of the cardiac rhythm monitored by the ECG monitor.

Optionally, the defibrillation advisory controller may further derive an electrical cardiac status of the patient inclusive of the cardiac rhythm monitored by the ECG monitor, and generate the defibrillation advisory based on the cardiac rhythm status the metabolic cardiac status and the electrical cardiac status of the patient.

For purposes of the present invention, the term "defibrillation advisory" broadly encompasses an official notice of whether or not to apply a defibrillation shock to the patients' heart and may take any form suitable for a particular medical device/system that may include, but is not limited to, a textual/graphical display, an audible notice and a charging/non-charging indication.

For purposes of the present invention, the term "cardiac rhythm status" broadly encompasses all heart conditions known to be suitable for defibrillation including, but not limited to, ventricular fibrillation ("VF") and ventricular tachycardia ("VT") (herein known as "shockable cardiac rhythms") and further broadly encompasses all heart conditions known not to be suitable for defibrillation including, but not limited to, asystole, a normal sinus rhythm, and supraventricular tachycardia (herein known as "non-shockable cardiac rhythms").

For purposes of the present invention, the term "metabolic cardiac status" broadly encompasses an indication whether the aerobic metabolism of a patient's heart supports a return of spontaneous circulation ("ROSC") by the patient's heart, and the phrase "derived exclusive of the shockable cardiac rhythm" broadly encompasses the aerobic metabolism not being derived from the cardiac rhythm of a patient's heart.

For purposes of the present invention, the term "ECG monitor" broadly encompasses all known monitors for generating and displaying (i.e., monitoring) an ECG of the patient's heart including, but not limited to, monitors incorporated within Philips Heartstart MRx, Philips Heartstart XL+ and Philips Efficia DFM 100.

For purposes of the present invention, the term "defibrillation advisory controller" broadly encompasses all structural configurations of an application specific main board or an application specific integrated circuit housed within or linked to a medical device/system for controlling an application of various inventive principles of the present invention as subsequently described herein. The structural configuration of the controller may include, but is not limited to, processor(s), computer-usable/computer readable storage medium(s), an operating system, application module(s), peripheral device controller(s), slot(s) and port(s).

For purposes of the present invention, the term "application module" broadly encompasses a component of the defibrillation advisory controller consisting of an electronic circuit or an executable program (e.g., executable software and/or firmware) for executing a specific application.

The defibrillation advisory controller may be incorporated with an ECG monitor or a defibrillator, and ECG monitor and a defibrillator may be modular or integrated components of the system.

For purposes of the present invention, the term "defibrillator" broadly encompasses all known defibrillator device and systems for delivering a defibrillation shock to a patient's heart including, but not limited to, defibrillators incorporated within Philips Heartstart MRx, Philips Heartstart XL+ and Philips Efficia DFM 100.

The defibrillation advisory controller may compute or receive metabolic cardiac data indicative of the metabolic cardiac status (e.g., incorporating or coupled to a user input device, a breath analyzer and/or a blood analyzer), and may compare the metabolic cardiac data to a metabolic cardiac threshold and/or monitor a trend of the metabolic cardiac data to derive the metabolic cardiac state of the patient.

For purposes of the present invention, the term "user input device" broadly encompasses all known user input devices including, but not limited to, a keyboard, a keypad and a graphical user interface.

For purposes of the present invention, the term "breath analyzer" broadly encompasses and descriptively labels all known breath analyzers for sampling a patient's breath for an indication of an aerobic metabolism of the patient's heart including, but not limited to, $CO_2$ monitors and $O_2$ monitors.

For purposes of the present invention, the term "blood analyzer" broadly encompasses and descriptively labels all known blood analyzers for sampling a patient's blood, directly or indirectly, for an indication of an aerobic metabolism of the patient's heart including, but not limited to, blood lactate testers, blood pH level testers, blood gas testers and plethysmographic monitoring.

A second form of the present invention is a defibrillation advisory controller employing application modules including a cardiac rhythm analyzer, a metabolic cardiac analyzer and a defibrillation advisor. In operation, the cardiac rhythm analyzer derives a cardiac rhythm status of a patient. The metabolic cardiac analyzer derives a metabolic cardiac status of the patient exclusive of a cardiac rhythm of the patient. And, the defibrillation advisor generates a defibrillation advisory responsive to the cardiac rhythm status and the metabolic cardiac status of the patient.

For this stand-alone form of the controller, the cardiac rhythm of the patient may be provided to the cardiac rhythm analyzer by an ECG monitor as previously stated herein or an alternative non-ECG source, particularly non-ECG sources capable of detecting a strong pulsatile waveform that may indicate a non-shockable rhythm for defibrillation purposes. Examples of non-ECG sources include, but are not limited to, invasive blood pressure, impedance plethysmography and photoplethysmography.

The defibrillation advisory controller may optionally employ an electrical cardiac analyzer to derive an electrical cardiac status of the patient inclusive of the cardiac rhythm of the patient whereby the defibrillation advisor generates a defibrillation advisory responsive to the cardiac rhythm status, the metabolic cardiac status of the patient and the electrical cardiac status of the patient. For the purposes of the present invention, any estimation of metabolic status of the cells derived solely from the electrical activity of the cells is considered a form of electrical cardiac status, and thus is considered exclusive of the cardiac rhythm of the patient.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF THE PREFERRED EMBODIMENTS

Figure 1:
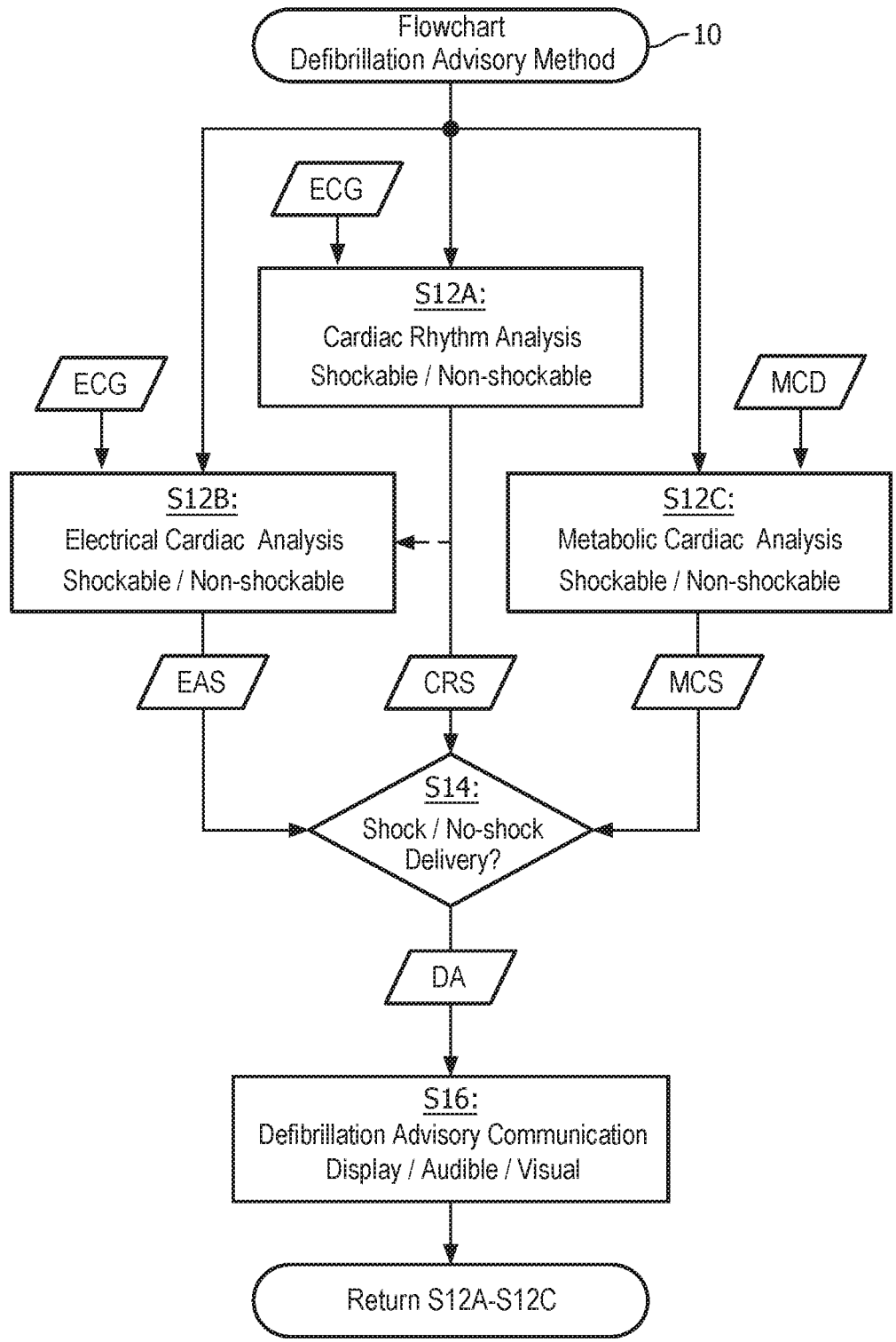
FIG. 1 illustrates a flowchart representative of an exemplary embodiment of a defibrillation advisory method in accordance with the inventive principles of the present invention.

To facilitate an understanding of the present invention, the following description of FIG. 1 teaches basic inventive principles of an exemplary defibrillation advisory method.

Of importance to note is the exemplary description herein is directed to an incorporation of an electrical cardiac status with a cardiac rhythm status and a metabolic cardiac status for a complete exemplary description. Nonetheless, in practice, the electrical cardiac status may be omitted for defibrillation advisory purposes.

Also of importance to note is various components are illustrated and described herein as separate and distinct components for clarity in describing the components. Nonetheless, in practice, such components may be housed in the same device and even further implemented by the same hardware and/or within the same software/firmware.

Referring to FIG. 1, a flowchart 10 represents a defibrillation advisory method for determining a prediction of a successful defibrillation. Upon initiation, process stages S12A-S12C are executed in parallel to provide input to a decision stage S14.

Specifically, process stage S12A encompasses a cardiac rhythm analysis derived from ECG data as known in the art and resulting in a cardiac rhythm status CRS indicator of (1) a shockable cardiac rhythm (e.g. VF or VT) of the ECG signal or (2) a non-shockable cardiac rhythm (e.g., asystole) of the ECG signal.

Process stage S12B encompasses an electrical cardiac analysis derived from ECG data as known in the art and resulting in an electrical cardiac status ECS indicator of (1) electrical activity of the ECG signal likely to support a return of spontaneous circulation ("ROSC") or (2) electrical activity of the ECG signal, if any, unlikely to support ROSC. Examples of predictive features of electrical activity within the ECG signal electrical activity as known in the art include, but are not limited to, amplitude range, average P-P amplitude, mean amplitude, amplitude spectrum analysis, peak frequency, centroid frequency, spectral flatness measure, energy, maximum power, centroid power, power spectrum analysis, mean slope and median slope.

Process stage S12C encompasses a metabolic cardiac analysis derived from metabolic cardiac data MCD independent of the ECG signal and resulting in a metabolic cardiac status MCS indicator of (1) cardiac aerobic metabolism likely to support ROSC, or (2) cardiac aerobic metabolism, if any, unlikely to support ROSC. Examples of predictive metabolic cardiac data include, but are not limited to, end-tidal carbon dioxide $CO_2$, and lactate and pH concentration in blood.

Decision stage S14 encompasses a decision whether or not a defibrillation shock should be delivered to the patient based on a combination of cardiac rhythm status CRS, electrical cardiac status ECS and metabolic cardiac state MCS and results in a defibrillation advisory DA of (1) a decision to recommend shock delivery decision or a (2) a decision not to recommend shock delivery. More particularly, if the ECG signal indicates a shockable cardiac rhythm and support for ROSC AND the metabolic cardiac data MCD independent of the ECG signal also supports ROSC, the combination of statuses provides a prediction for a successful defibrillation that results in a decision to recommend shock delivery. Otherwise, if the ECG signal indicates a non-shockable cardiac rhythm and/or fails to support ROSC OR the metabolic cardiac data MCD independent of the ECG signal also fails to support ROSC, the combination of statuses provides a prediction of an unsuccessful defibrillation that results is a decision not to recommend shock delivery.

A process stage S16 of flowchart 10 encompasses a communication of defibrillation advisory DA that may include, but is not limited to, a textual/graphical display (particularly in conjunction with an ECG display), an audible message, and a visual indication of a charging or non-charging of a shock source. A reaction to a communication ranges from an acknowledgment that a shock will likely restore a pulsatile rhythm (i.e., shock delivery) to the initiation or continuation of chest compressions or termination of resuscitation efforts (i.e., non-shock delivery).

Process stage S16 returns to stages S12A-S12C until termination of flowchart 10.

Figure 2:
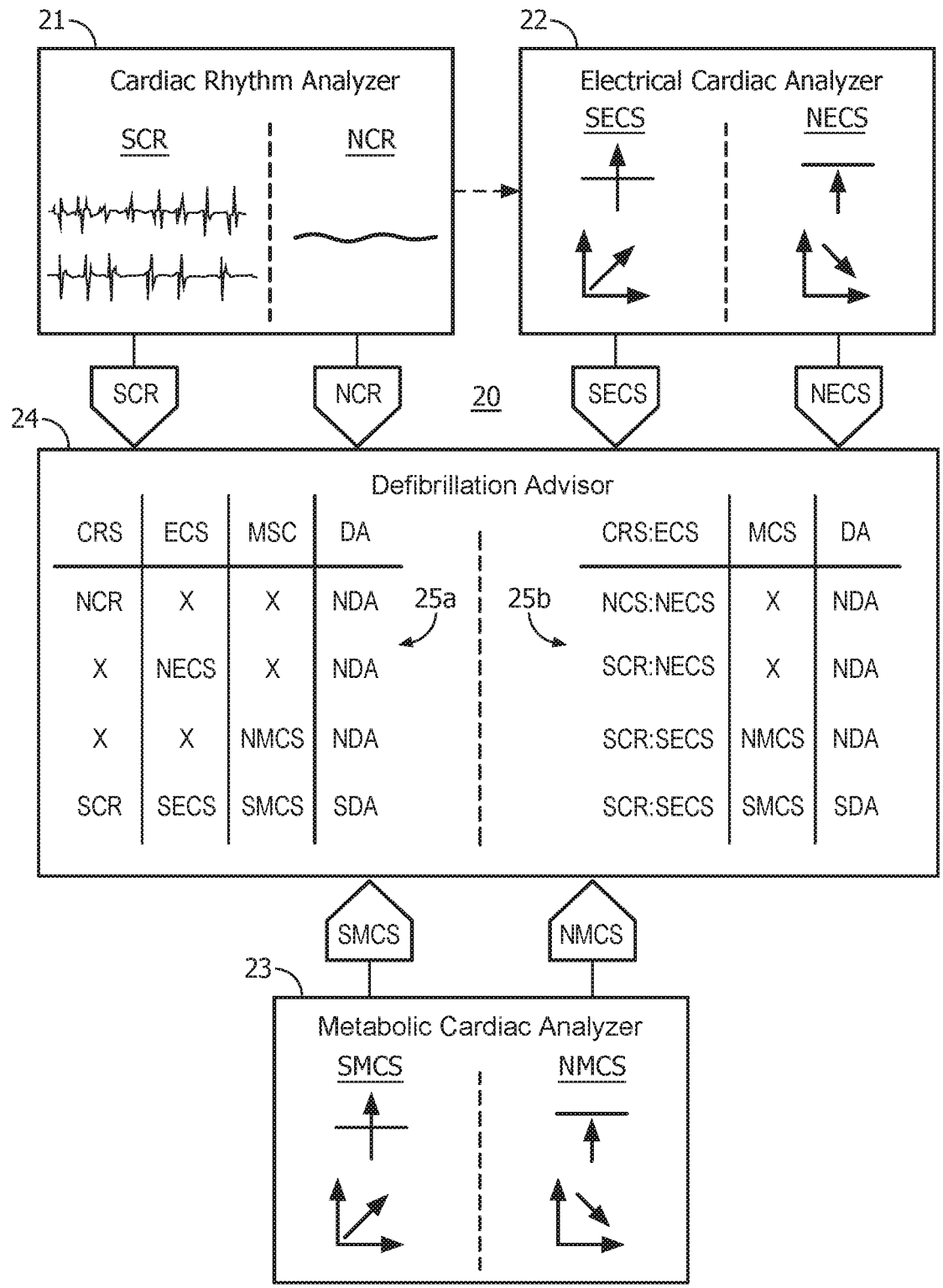
FIG. 2 illustrates a block diagram of an exemplary embodiment of a defibrillation advisory controller in accordance with the inventive principles of the present invention.

To further facilitate an understanding of the present invention, the following description of FIG. 2 applies the basic inventive principles of FIG. 1 to an exemplary defibrillation advisory controller 20.

Referring to FIG. 2, defibrillation advisory controller 20 employs a cardiac rhythm analyzer 21, an electrical cardiac analyzer 22, a metabolic cardiac analyzer 23 and a defibrillation advisor 24.

Cardiac rhythm analyzer 21 executes known techniques for analyzing ECG data (FIG. 1) to ascertain if the ECG data indicates a shockable cardiac rhythm SCR (e.g., VF and VT as symbolically shown) or a non-shockable cardiac rhythm NCR (e.g., asystole as symbolically shown).

Electrical cardiac analyzer 22 analyzes predictive features of ECG data (FIG. 1) to ascertain if the ECG data indicates a shockable electrical cardiac state SECS supportive of a ROSC or a non-shockable electrical cardiac state unsupportive of a ROSC.

In one embodiment, electrical cardiac analyzer 23 compares an instantaneous measurement of a predictive feature to an electrical activity threshold whereby the predictive feature exceeding the electrical activity threshold as symbolically shown indicates support for ROSC and whereby the predictive feature being less than the electrical activity threshold as symbolically shown fails to indicate support for ROSC.

For example, an amplitude spectrum analysis ("AMSA") of the ECG data may be compared to an electrical activity threshold of 1.75.

Alternatively, the predictive feature exceeding the electrical activity threshold fails to indicate support for ROSC, and the predictive feature being less than the electrical activity threshold indicates support for ROSC.

In practice, the electrical activity threshold for each predictive feature should be chosen to balance sensitivity (aggressive defibrillation) versus specificity (aggressive compression), and may be fixed or variable.

Also in practice, a combination of multiple predictive features may be analyzed for determining support or non-support of ROSC. For such combinations, the predictive features may or may not be equally weighted.

In another embodiment, electrical cardiac analyzer 22 analyzes a trend of a predictive feature as symbolically shown whereby an upward trend of the predictive feature as symbolically shown indicates support for ROSC and whereby a downward trend of the predictive feature as symbolically shown fails to indicate support for ROSC.

Alternatively, an upward trend but low value of the predictive feature can indicate a delay in recommending a shock to allow additional recovery would better support ROSC, and a downward trend with a high value of the predictive feature indicates recommending an early shock would give better support for ROSC.

In practice, the conditions for determining a trend should be chosen to balance sensitivity (aggressive defibrillation) versus specificity (aggressive compressions).

Again in practice, a combination of multiple predictive features may be analyzed for determining support or non-support of ROSC. For such combinations, the predictive features may or may not be equally weighted.

Metabolic cardiac analyzer 23 analyzes predictive features of metabolic cardiac data MCD (FIG. 1) independent of ECG data (FIG. 1) to ascertain if the metabolic cardiac data MCD indicates a shocking metabolic cardiac state SMCS supportive for a ROSC or a non-shocking metabolic cardiac state NMCS unsupportive of a ROSC.

In one embodiment, metabolic cardiac analyzer 23 compares an instantaneous measurement of a predictive feature to an aerobic metabolism threshold whereby the predictive feature exceeding the aerobic metabolism threshold as symbolically shown indicates support for ROSC and whereby the predictive feature being less than the aerobic metabolism threshold as symbolically shown fails to indicate support for ROSC.

For example, a partial pressure of end-tidal $CO_2$ may be compared to an aerobic metabolism threshold of 10 mmHg.

Alternatively, the predictive feature exceeding the aerobic metabolism threshold fails to indicate support for ROSC, and the predictive feature being less than the metabolic threshold indicates support for ROSC.

In practice, the aerobic metabolism threshold for each predictive feature should be chosen to balance sensitivity (aggressive defibrillation) versus specificity (aggressive compression), and may be fixed or variable.

Also in practice, a combination of multiple predictive features may be analyzed for determining support or non-support of ROSC. For such combinations, the predictive features may or may not be equally weighted.

In another embodiment, metabolic cardiac analyzer 23 analyzes a trend of a predictive feature as symbolically shown whereby an upward trend of the predictive feature as symbolically shown indicates support for ROSC and whereby a downward trend of the predictive feature as symbolically shown fails to indicate support for ROSC.

Alternatively, an upward trend but low value of the predictive feature can indicate a delay in recommending a shock to allow additional recovery would better support ROSC, and a downward trend with a high value of the predictive feature indicates recommending an early shock would give better support for ROSC.

In practice, the conditions for determining a trend should be chosen to balance sensitivity (aggressive defibrillation) versus specificity (aggressive compression).

Again in practice, a combination of multiple predictive features may be analyzed for determining support or non-support of ROSC. For such combinations, the predictive features may or may not be equally weighted.

Defibrillator advisor 24 combines signals from analyzers 21-23 to decide whether to communicate defibrillation advisory DA as (1) a shocking delivery decision or (2) a non-shocking delivery decision.

In practice, signals from analyzers 21-23 may be combined by defibrillator advisor 24 in any manner determined to yield a successful prediction for a defibrillation.

In one embodiment, defibrillator advisor 24 applies a logical chart 25a whereby each signal from analyzer 21-23 is utilized as an input signal.

For this embodiment, if (1) cardiac rhythm analyzer 21 outputs a non-shocking cardiac rhythm NCR or (2) electrical cardiac analyzer 22 outputs a non-shocking electrical cardiac state NECS or (3) metabolic cardiac analyzer 23 outputs a non-shocking metabolic cardiac state NMCS, then defibrillator advisor 24 communicates the defibrillation advisory DA as a non-shocking defibrillation advisory NDA.

Otherwise, if (1) cardiac rhythm analyzer 21 outputs a shocking cardiac rhythm CCR and (2) electrical cardiac analyzer 22 outputs a hocking electrical cardiac state SECS and (3) metabolic cardiac analyzer 23 outputs a shocking metabolic cardiac state SMCS, then defibrillator advisor 24 communicates the defibrillation advisory DA as a shocking defibrillation advisory SDA.

In another embodiment, defibrillator advisor 24 applies a logical chart 25b whereby the signal from cardiac rhythm analyzer 21 is used as an enabling signal for electrical cardiac analyzer 22.

For this embodiment, if cardiac rhythm analyzer 21 outputs a non-shocking cardiac rhythm NCR, then electrical cardiac analyzer 22 is disabled and automatically outputs a non-shocking electrical cardiac state NECS, which results in defibrillator advisor 24 communicates the defibrillation advisory DA as a non-shocking defibrillation advisory NDA.

Otherwise, if cardiac rhythm analyzer 21 outputs a shocking cardiac rhythm SCR, then electrical cardiac analyzer 22 is enabled whereby defibrillator advisor 24 communicates the defibrillation advisory DA as a non-shocking defibrillation advisory NDA if (1) electrical cardiac analyzer 22 outputs a non-shocking electrical cardiac state NECS or (2) metabolic cardiac analyzer 23 outputs a non-shocking metabolic cardiac state NMCS, or whereby defibrillator advisor 24 communicates the defibrillation advisory DA as a shocking defibrillation advisory SDA if (1) electrical cardiac analyzer 22 outputs a shocking electrical cardiac state SECS and (2) metabolic cardiac analyzer 23 outputs shocking metabolic cardiac state SMCS.

Figure 3A:
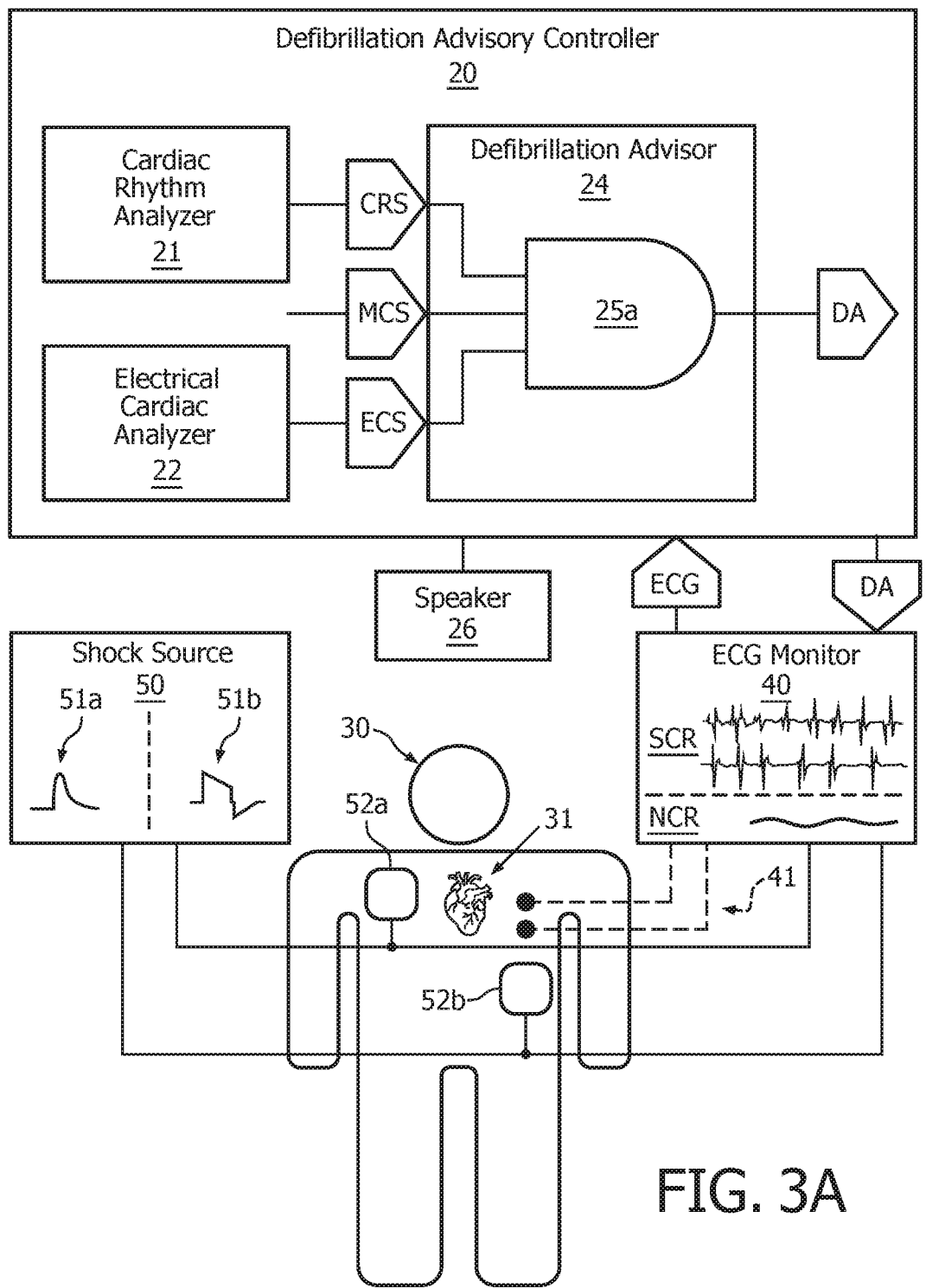
FIGS. 3A and 3B illustrate a block diagram of an exemplary embodiment of a system in accordance with the inventive principles of the present invention.
Figure 3B:
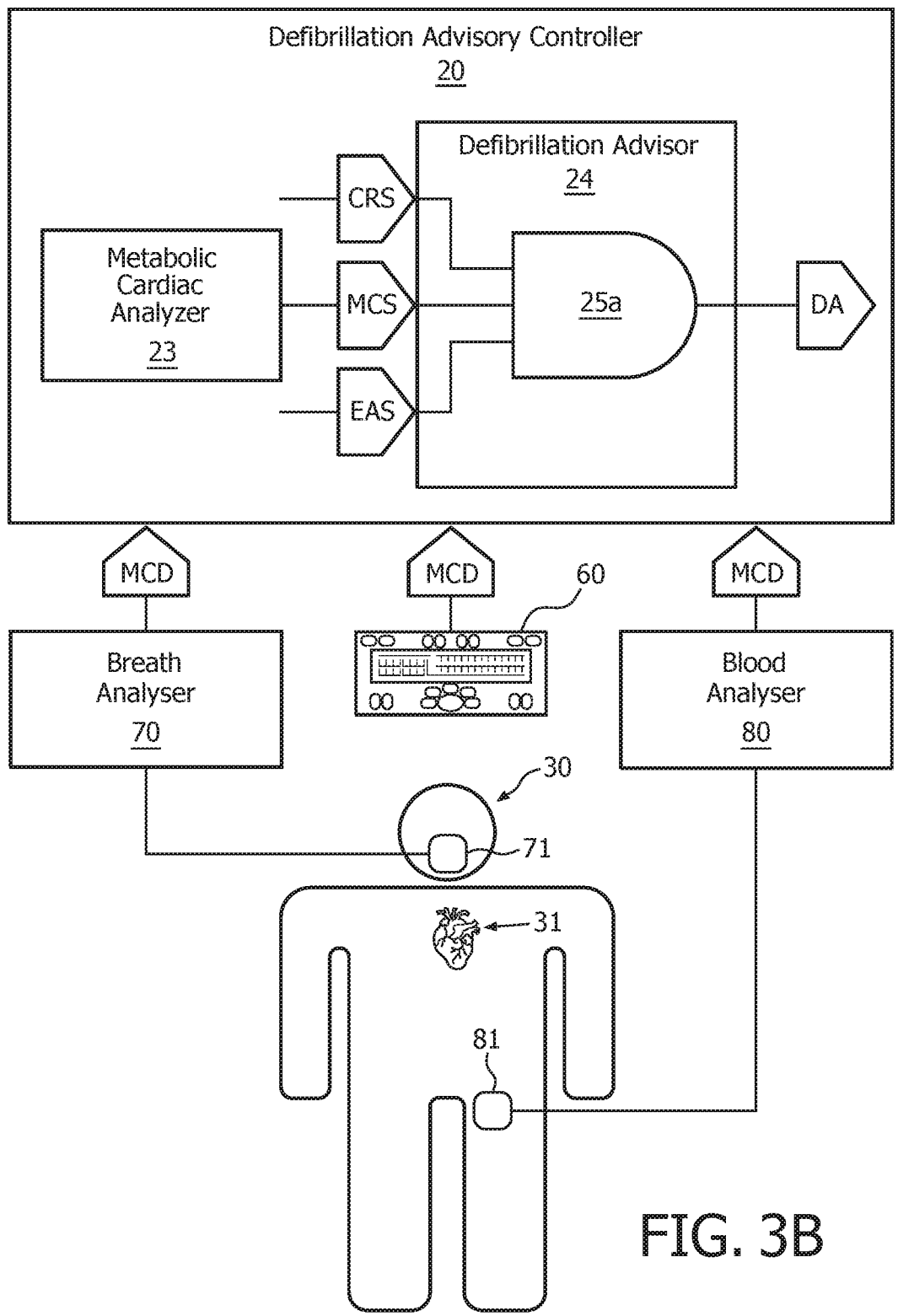

To even further facilitate an understanding of the present invention, the following description of FIGS. 3A and 3B incorporates the defibrillation advisory controller of FIG. 2 into an exemplary medical system.

Referring to FIGS. 3A and 3B, the medical system employs defibrillation advisory controller 20, a speaker 26, an ECG monitor 40, optional ECG leads 41 (e.g., a 12-lead system), shock source 50, a pair of electrode pad/paddles 52, a user input device in the form of a keyboard 60, a breath analyzer 70, a breathing device 71, a blood analyzer 80 and a catheter 81.

An ECG analyzing partition of defibrillation advisory controller 20 as shown in FIG. 3A incorporates cardiac rhythm analyzer 21 (FIG. 2) and electrical cardiac analyzer 22 (FIG. 2) applying respective CRS and ECS signals to defibrillation advisor 24 (FIG. 2) implementing flowchart 25a executable as an AND gate in circuit or software form.

A metabolic analyzing partition of defibrillation advisory controller 20 as shown in FIG. 3B incorporates metabolic cardiac analyzer 23 (FIG. 2) applying MCS signal to defibrillation advisor 24.

Referring to FIG. 3A, electrode pads/paddles 52 are structurally configured as known in the art to be conductively applied to a patient 30 in an anterior-apex arrangement as shown in FIG. 3A or in an anterior-posterior arrangement (not shown). Electrode pads/paddles 52 conduct a defibrillation shock from shock source 50 to a heart 31 of patient 30 as controlled by defibrillation advisory controller 25, and conduct electrical activity of heart 31 of patient 30 to ECG monitor 40. Alternatively or concurrently, ECG leads 33 as known in the art (e.g., limb-lead set, 12-lead set) may be connected to patient 30 to conduct the electrical activity of heart 31 of patient 30 to ECG monitor 40.

ECG monitor 40 is structurally configured as known in the art to measure an ECG waveform of heart 31 of patient 30 as an indication patient 30 is experiencing a shockable cardiac rhythm SCR (e.g., VF or VT) or a non-shockable cardiac rhythm NCR (e.g., asystole or normal sinus rhythm).

In one embodiment, ECG monitor 40 employs a digital signal processor (not shown) for streaming ECG data to defibrillation advisory controller 20 for analysis by cardiac rhythm analyzer 21 and electrical cardiac analyzer 22.

Shock source 50 is structurally configured as known in the art to store electric energy for delivery of a defibrillation shock 51 via electrode pads/paddles 52 to heart 31 of patient 30 as controlled by defibrillation advisory controller 25. In practice, defibrillation shock 51 may have any waveform as known in the art. Examples of such waveforms include, but are not limited to, a monophasic damped sinusoidal waveform (positive sine wave) 51a and a biphasic truncated exponential waveform 51b as shown in FIG. 3A.

In one embodiment, shock source 50 employs a high voltage capacitance (not shown) for storing a high voltage via a high voltage charger and a power supply upon a pressing of a charge button. Shock source 50 further employs a switching/isolation circuit (not shown) for selectively applying a specific waveform of an electric energy charge from the high voltage capacitance to electrode pads/paddles 52.

Referring to FIG. 3B, keyboard 60, breath analyzer 70, and blood analyzer 80 provide metabolic cardiac data MCD to defibrillation advisory controller 20 for analysis by metabolic cardiac analyzer 23. More particularly, keyboard 60 is utilized to input metabolic cardiac data MCD obtained by user measurements of aerobic metabolism of patient 30 including, but not limited to, end-tidal carbon dioxide $CO_2$, and lactate and pH concentration in blood. Breath analyzer 70 via a breathing device 71 directly provides metabolic cardiac data MCD from exhalations by patient 30 including, but not limited to, end-tidal carbon dioxide $CO_2$. Blood analyzer 80 via catheter 81 provides metabolic cardiac data MCD from blood samples by patient 30 including, but not limited to, $CO_2$, $O_2$, lactate and pH concentration in blood. More particularly, catheter 81 is inserted through a femoral artery accessed in the thigh/crotch area whereby blood samples are drawn and analyzed with a point of care (POC) device that is connected to the system. Alternatively, blood monitoring could be done with electrodes placed in the flow of blood during an extracorporeal membrane oxygenation (ECMO) procedure.

Referring to FIGS. 3A and 3B, defibrillation advisory controller 20 may be practiced in an unlimited variety of medical device/system configurations.

In one embodiment, defibrillation advisory controller 20 may be a separate modular component within a medical system from ECG monitor 40, shock source 50, breath analyzer 70 and blood analyzer 80 as shown in FIGS. 3A and 3B (e.g., a modular advanced defibrillator/monitor). For this embodiment, defibrillation advisory controller 20 may or may not be incorporated with a master controller for the medical device/system.

In a second embodiment, defibrillation advisory controller 20 and ECG monitor may be incorporated within the same medical device that may or may not be a component of a medical system (e.g., an automated external defibrillator).

In a third embodiment, defibrillation advisory controller 20 and shock source 50 may be incorporated within the same medical device that may or may not be a component of a medical system (e.g., an automated external defibrillator).

In a fourth embodiment, breath analyzer 70 and/or blood analyzer 80 may or may not be integrated into defibrillation advisory controller 20, or may be incorporated with defibrillation advisory controller 20 within a master controller.

Referring to FIGS. 1-3, those having ordinary skill in the art will appreciate numerous benefits of the present invention including, but not limited to, a higher percentage of successful defibrillation shocks and resuscitation attempts, shorter resuscitation times, reduced chance of injury from inappropriate shocks and/or longer times to achieving ROSC, and reduced rescuer fatigue through shorter resuscitation times.

Furthermore, as one having ordinary skill in the art will appreciate in view of the teachings provided herein, features, elements, components, etc. described in the present disclosure/specification and/or depicted in the FIGS. 1-3 may be implemented in various combinations of electronic components/circuitry, hardware, executable software and executable firmware, particularly as application modules of a controller as described herein, and provide functions which may be combined in a single element or multiple elements. For example, the functions of the various features, elements, components, etc. shown/illustrated/depicted in the FIGS. 1-3 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of novel and inventive system and method for predicting a successful defibrillation, (which embodiments are intended to be illustrative and not limiting), it is noted that modifications and variations can be made by persons having ordinary skill in the art in light of the teachings provided herein, including the FIGS. 1-3. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. A system, comprising:
an ECG monitor operable to monitor a cardiac rhythm of a patient; and
a defibrillation advisory controller in electrical communication with the ECG monitor, the defibrillation advisory controller configured to:
derive a cardiac rhythm status of the patient as monitored by the ECG monitor;
receive metabolic cardiac data indicative of a metabolic cardiac status of the patient;
derive the metabolic cardiac status of the patient without using the cardiac rhythm monitored by the ECG monitor; and
generate a defibrillation advisory based on the derived cardiac rhythm status and the metabolic cardiac status of the patient derived without using the cardiac rhythm monitored by the ECG monitor;
wherein the defibrillation advisory controller is configured to derive the metabolic cardiac status by comparing the metabolic cardiac data to an aerobic metabolism threshold; and
wherein the ECG monitor and the defibrillation advisory controller are disposed external to the patient.

2. The system of claim 1, wherein the defibrillation advisory controller generates the defibrillation advisory as a non-shocking defibrillation advisory responsive to at least one of:
the cardiac rhythm status indicating a non-shockable electrical cardiac rhythm of the patient; and
the metabolic cardiac status indicating a non-shockable metabolic cardiac state of the patient.

3. The system of claim 1, wherein the defibrillation advisory controller generates the defibrillation shock advice as a shocking defibrillation advisory responsive to both:
the cardiac rhythm status indicating a shockable cardiac rhythm of the patient; and
the metabolic cardiac status indicating a shockable metabolic cardiac state of the patient.

4. The system of claim 1,
wherein the defibrillation advisory controller is further operable to derive an electrical cardiac status of the patient inclusive of the cardiac rhythm monitored by the ECG monitor; and
wherein the defibrillation advisory controller generates the defibrillation advisory based on the cardiac rhythm status, the metabolic cardiac status and the electrical cardiac status of the patient.

5. The system of claim 4, wherein the defibrillation advisory controller generates the defibrillation advisory as a non-shocking defibrillation advisory responsive to at least one of:
the cardiac rhythm status indicating a non-shockable electrical cardiac rhythm of the patient;
the metabolic cardiac status indicating a non-shockable metabolic cardiac state of the patient; and
the electrical cardiac status indicating a non-shockable electrical cardiac state of the patient.

6. The system of claim 4, wherein the defibrillation advisory controller generates the defibrillation advisory as a shocking defibrillation advisory responsive to all of:
the cardiac rhythm status indicating a shockable electrical cardiac rhythm of the patient;
the metabolic cardiac status indicating a shockable metabolic cardiac state of the patient; and
the electrical cardiac status indicating a shockable electrical cardiac state of the patient.

7. The system of claim 1,
wherein the defibrillation advisory controller is operable to receive metabolic cardiac data indicative of the metabolic cardiac status of the patient; and
wherein the defibrillation advisory controller monitors a trend of the metabolic cardiac data to derive the metabolic cardiac status of the patient.

8. The system of claim 1, further comprising:
an user input device in electrical communication with the defibrillation advisory controller to provide metabolic cardiac data indicative of the metabolic cardiac status of the patient to the defibrillation advisory controller for deriving the metabolic cardiac status of the patient.

9. The system of claim 1, further comprising:
a breath analyzer operable to generate metabolic cardiac data indicative of the metabolic cardiac status of the patient derived from a breathing sample of the patient,
wherein the defibrillation advisory controller is operable in communication with the breath analyzer to receive the metabolic cardiac data for deriving the metabolic cardiac status of the patient.

10. The system of claim 1, further comprising:
a blood analyzer operable to generate the metabolic cardiac data indicative of the metabolic cardiac status of the patient derived from a blood sample of the patient,
wherein the defibrillation advisory controller is operable in communication with the blood analyzer to receive the metabolic cardiac data for deriving the metabolic cardiac status of the patient.

11. The system of claim 10, wherein the metabolic cardiac data indicative of the metabolic cardiac status of the patient derived from the blood sample of the patient comprises $CO_2$ concentration in the blood sample.

12. The system of claim 10, wherein the metabolic cardiac data indicative of the metabolic cardiac status of the patient derived from the blood sample of the patient comprises 02 concentration in the blood sample.

13. The system of claim 10, wherein the metabolic cardiac data indicative of the metabolic cardiac status of the patient derived from the blood sample of the patient comprises lactate concentration in the blood sample.

14. The system of claim 10, wherein the metabolic cardiac data indicative of the metabolic cardiac status of the patient derived from the blood sample of the patient comprises pH concentration in the blood sample.

15. A defibrillation method, comprising:
deriving a metabolic cardiac status of the patient exclusive of the derived cardiac rhythm by receiving metabolic cardiac data indicative of a metabolic cardiac status of the patient and comparing the metabolic cardiac data to an aerobic metabolism threshold to derive the metabolic cardiac status of the patient, the metabolic cardiac status being derived without the use of cardiac rhythm data;
monitoring a cardiac rhythm of a patient;

deriving a cardiac rhythm status of the patient; and generating a defibrillation advisory based on the derived cardiac rhythm status and the derived metabolic cardiac status of the patient;

wherein the deriving, the monitoring, the deriving, and the generating are performed by an ECG monitor and a defibrillation advisory controller disposed in a common automated external defibrillator device.

16. The method of claim 15, wherein generating the defibrillation advisory as a non-shocking defibrillation advisory is performed responsive to at least one of:

the cardiac rhythm status indicating a non-shockable electrical cardiac rhythm of the patient; and the metabolic cardiac status indicating a non-shockable metabolic cardiac state of the patient; and wherein the defibrillation shock advice as a shocking defibrillation advisory is generated responsive to both:

the cardiac rhythm status indicating a shockable cardiac rhythm of the patient; and the metabolic cardiac status indicating a shockable metabolic cardiac state of the patient.

17. The method of claim 15, further comprising:

deriving an electrical cardiac status of the patient inclusive of the cardiac rhythm of the patient, generating the defibrillation advisory based on the cardiac rhythm status, the metabolic cardiac status and the electrical cardiac status of the patient.

18. The method of claim 17, wherein the defibrillation advisory as a non-shocking defibrillation advisory is generated responsive to at least one of:

the cardiac rhythm status indicating a non-shockable electrical cardiac rhythm of the patient;

the metabolic cardiac status indicating a non-shockable metabolic cardiac state of the patient;

the electrical cardiac status indicating a non-shockable electrical cardiac state of the patient; and wherein the defibrillation shock advice as a shocking defibrillation advisory is generated responsive to all of:

the cardiac rhythm status indicating a shockable cardiac rhythm of the patient; and the metabolic cardiac status indicating a shockable metabolic cardiac state of the patient; and the electrical cardiac status indicating a shockable electrical cardiac state of the patient.

19. The method of claim 15, further comprising:

deriving the metabolic cardiac status of the patient by monitoring a trend of the metabolic cardiac data.

20. The method of claim 15, wherein the deriving of the metabolic cardiac status comprises deriving the metabolic cardiac status from received metabolic cardiac data comprising $CO_2$, $O_2$, lactate, and/or pH concentration in a blood sample of the patient.

* * * * *